United States Patent
Zimmerman

(10) Patent No.: US 7,247,837 B2
(45) Date of Patent: Jul. 24, 2007

(54) OPTICAL MOISTURE SENSOR AND METHOD OF MAKING THE SAME

(75) Inventor: James Zimmerman, Mahogany, CT (US)

(73) Assignee: The Toro Company, Bloomington, MN (US)

( * ) Notice: Subject to any disclaimer, the term of this patent is extended or adjusted under 35 U.S.C. 154(b) by 35 days.

(21) Appl. No.: 11/214,101

(22) Filed: Aug. 29, 2005

(65) Prior Publication Data

US 2006/0043270 A1    Mar. 2, 2006

Related U.S. Application Data

(60) Provisional application No. 60/605,178, filed on Aug. 27, 2004.

(51) Int. Cl.
 *G01N 21/01* (2006.01)
 *G01J 31/10* (2006.01)
(52) U.S. Cl. ............ 250/227.25; 250/573; 356/128; 340/603
(58) Field of Classification Search ......... 250/227.25, 250/573, 574; 356/128–137; 340/603, 604, 340/606, 618, 619
See application file for complete search history.

(56) References Cited

U.S. PATENT DOCUMENTS

| | | | | |
|---|---|---|---|---|
| 4,274,705 A | * | 6/1981 | Miller | 385/12 |
| 4,306,805 A | * | 12/1981 | Arrington | 356/133 |
| 4,422,714 A | * | 12/1983 | Benoit et al. | 385/39 |
| 4,803,470 A | * | 2/1989 | Fineman | 340/583 |
| 4,974,552 A | * | 12/1990 | Sickafus | 123/1 A |
| 5,442,435 A | * | 8/1995 | Cooper et al. | 356/133 |
| 6,690,452 B2 | * | 2/2004 | Wilks, Jr. | 356/70 |
| 6,855,947 B2 | * | 2/2005 | Graves et al. | 250/573 |
| 7,189,960 B2 | * | 3/2007 | Zimmerman | 250/227.25 |

* cited by examiner

*Primary Examiner*—John R. Lee
(74) *Attorney, Agent, or Firm*—Inskeep IP Group, Inc.

(57) ABSTRACT

A soil moisture sensor uses a non-collimated light source and a photosensor, respectively, mounted at the foci of a transparent ellipsoidal plastic body. The dimensions of the body are such that emitted light rays are internally reflected toward the photosensor at the surface of the ellipsoid if the surface is dry, but refracted outwardly of the body when the surface is wet. The amount of light reflected onto the photosensor is thus a measure of the amount of moisture at the surface of the sensor. Direct illumination of the photosensor by the light source is prevented either by interposing opaque electronic components between them on a circuit board, or by taking advantage of light source characteristics to minimize the amount of transmitted light. If a circuit board is used, it is completely encapsulated against moisture penetration by fixing it in a carrier and molding the body around and onto the carrier to form a monolithic unit with the carrier and circuit board.

12 Claims, 7 Drawing Sheets

OPTICAL MOISTURE SENSOR AND METHOD OF MAKING THE SAME

RELATED APPLICATIONS

This application claims priority to U.S. Provisional Application Ser. No. 60/605,178 filed Aug. 27, 2004 entitled Optical Moisture Sensor and Method of Making the Same and is hereby incorporated by reference.

FIELD OF THE INVENTION

This invention relates to optical moisture sensors for irrigation systems, and more particularly to a soil moisture sensor using a solid, transparent ellipsoidal body with a non-collimated light source embedded at one of its foci to reflect light toward a photosensor embedded at the other focus of the body if the soil contacting the surface of the body is dry, or to refract it outwardly of the body if the soil is wet.

BACKGROUND OF THE INVENTION

Optical sensors for determining the moisture content of the soil in an irrigation system are well known. They usually take the form of a prism or similar structure, in which a light beam projected into the prism is internally reflected toward a photosensor such as a photodiode or phototransistor. (The term "light" in this application is meant to include infrared radiation). The amount of light received by the photosensor depends on the amount of moisture present at the surfaces of the prism. This moisture changes the optical characteristics of the prism surface and thereby causes a portion of the beam to be refracted outwardly of the prism, instead of being reflected inwardly toward the light sensor. The amount of refraction, and thus the amount of light received by the photosensor, translates into a measurement of the wetness of the soil.

It has previously been proposed in Benoit et al. U.S. Pat. No. 4,422,714 to use a transparent half-ellipsoid body as a level sensor in a container of mineral oil. In that patent, a fiber-optic light guide conveying substantially collimated light from a light source to the ellipsoid's surface is terminated at one of the foci of the ellipsoid, while a second light guide conveying light to a photosensor receives similarly collimated reflected light at the other focus of the ellipsoid. If all or part of the convex surface of Benoit's body is immersed in mineral oil, the resulting change in the index of refraction at the body-oil interface causes the light received by the photosensor to indicate not only the presence of a critical oil level but also whether it is rising or falling.

The above-described prior art construction is not, however, practical for soil moisture sensors because the presence of particulates in soil requires using the maximum available surface area of the ellipsoidal body as a reflection surface, so as to average the moisture effects over as large a surface of the sensor body as possible. This in turn requires a wide-angle light source and a wide-angle photosensor at the foci of the ellipsoid. One solution to this problem is shown in my copending application Ser. No. 11/214,100, filed on Aug. 29, 2005 and entitled Optical Moisture Sensor the contents of which are hereby incorporated by reference. That application discloses a cylindrical sensor with an interior refracting surface that causes divergent light rays to be refracted into parallelism so as to make optimum use of the cylindrical soil-contacting surface of the sensor.

A disadvantage of the sensor shown in the above-cited copending application in cold and moist environments is the fact that an air space needs to exist between the light source or photosensor and the internal refracting surface. In a cold environment, condensation can occur in that air space, and in a very moist environment, moisture can migrate through the sensor material. In either event, these conditions may adversely affect the parallelism of the internally refracted rays and may require special manufacturing precautions.

The aforesaid disadvantage can be overcome by mounting a wide-angle light source and photosensor in direct contact with a transparent ellipsoidal body. This does, however, cause several other problems. For one, a substantial portion of the light travels directly through the transparent body from the light source to the photosensor without being reflected by any body-air or body-water interface. Consequently, the sensitivity of such a sensor is substantially compromised.

Another problem arises in the manufacture of moisture sensors of the type described due to the fact that the light source and photosensor must be maintained in exact alignment with the foci of the ellipsoid during manufacture. This is necessary in order to produce consistent readings among mass-produced sensors. Also, the difference in coefficients of expansion between the body material and the circuit board on which the sensor's optical and electronic components are typically mounted can cause minute cracks adjacent the board into which moisture can migrate. It is therefore necessary to so encapsulate the light source, photosensor and associated electronics in the ellipsoidal body that moisture cannot cause any discontinuities between them and the body.

SUMMARY OF THE INVENTION

The invention solves the first problem mentioned above by mounting some of the non-light related circuit components (e.g. resistors, capacitors and chips) of the moisture-sensing electronics on the circuit board between the light source and photosensor so that they prevent any non-reflected light from reaching the photosensor.

The invention solves the second problem by providing a plastic carrier that firmly secures and aligns the circuit board with respect to the mold in which the transparent ellipsoidal body of the sensor is formed, yet allows the body material to completely surround the board without any air interface in the light path, and to form a moisture-tight bond with the carrier in the finished unit.

DESCRIPTION OF THE PREFERRED EMBODIMENT

Figure 1A:
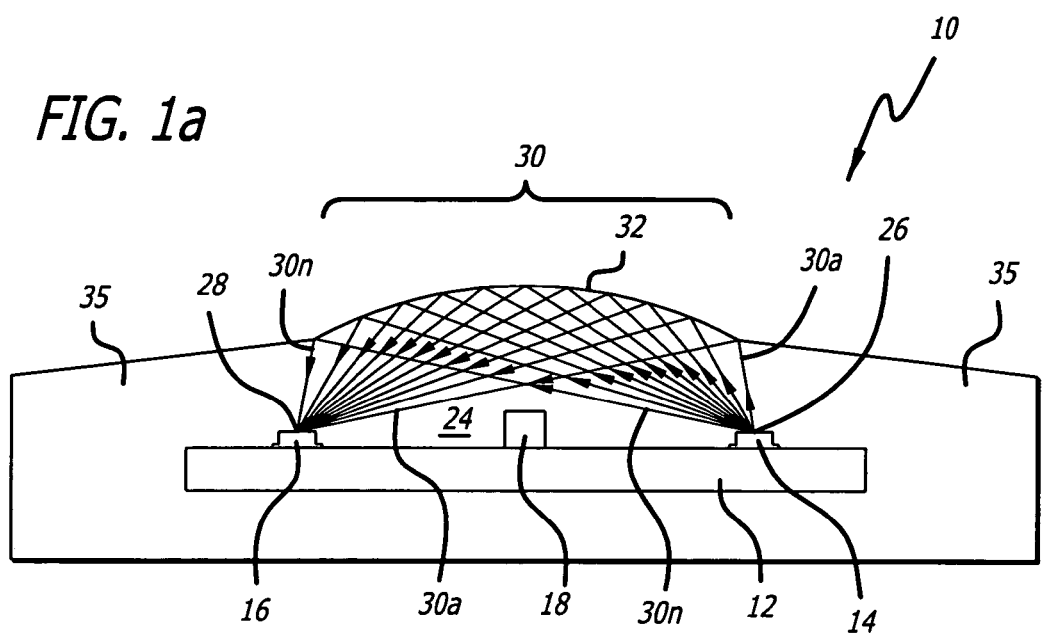
FIGS. 1a and 1b are schematic vertical sections along the axis of the inventive ellipsoidal moisture sensor illustrating the optical functioning of the sensor in dry and wet soils, respectively.
Figure 1B:
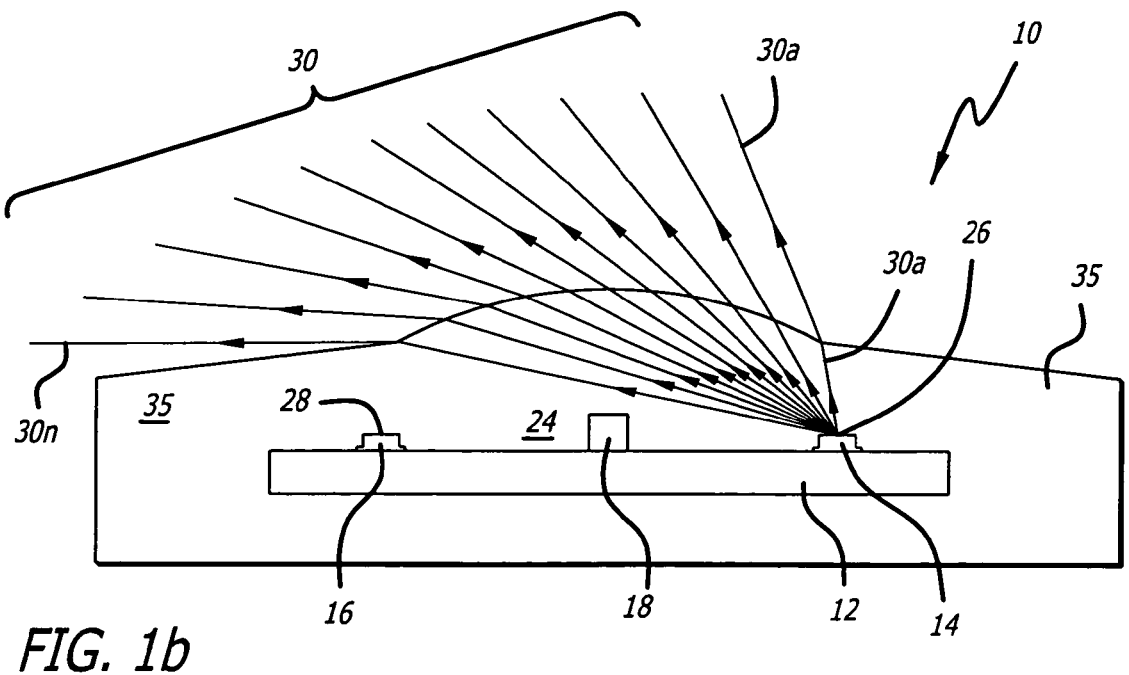

FIGS. 1a and 1b illustrate the functioning of the invention. The sensor 10 consists of a circuit board 12 carrying a light source such as, e.g., an infrared emitting diode (IRED) 14, a light sensing device such as, e.g., a photosensor 16, and a component package 18. The components of the package 18 may, for example, include transformers, capacitors and/or resistors, or other components suitable for causing the IRED 14 to produce appropriate illumination and to cause the illumination received by the photosensor 16 to be translated into usable signals. In accordance with the invention, the package 18 is positioned on the circuit board 12 between the IRED 14 and the photosensor 16. The package 18 is opaque and taller than the elevation of the IRED 14 and photosensor 16 with respect to the circuit board 12, so as to shade the photosensor 16 from direct illumination by the IRED 14.

Figure 1C:
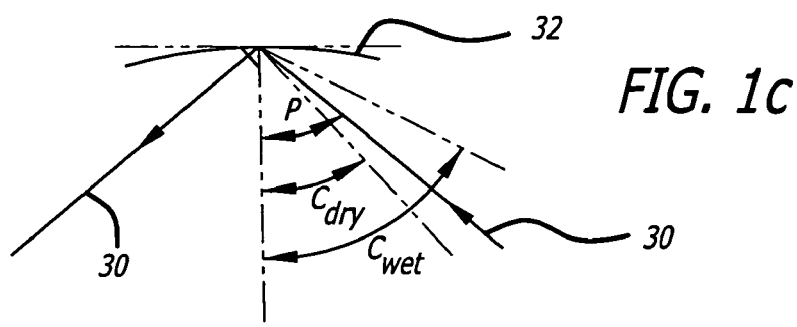
FIG. 1c is a diagram illustrating the critical angles at the surface of the ellipsoidal body of the sensor of FIGS. 1a and 1b.

An ellipsoidal body 24 of a transparent plastic such as cyclic olefin copolymer (COC) or acrylic polymer is formed over, and in intimate contact with, the circuit board 12 and the IRED 14, photosensor 16 and package 18 positioned thereon. The IRED 14 and the photosensor 16 are wide-angle devices and are positioned, respectively, at the two foci 26 and 28 of the ellipsoidal body 24. Therefore, any rays emitted by the IRED 14 between the limit rays 30a and 30n are reflected at the ellipsoidal surface 32 of the body 24 toward the photosensor 16 as long as they impinge upon the surface 32 at an angle greater than the critical angle $C_{dry}$ (FIG. 1c) if the surface 32 is dry, or the critical angle $C_{wet}$ if the surface 32 is wet. For acrylic as the body material, $C_{dry}$ is 42.16°, and $C_{wet}$ is 63.20°.

Thus, the dimensions of the ellipsoidal body 24 must be such that all rays 30 between the limit rays 30a and 30n impinge upon the ellipsoidal surface 32 at an angle P between about 43° and 63°, which is greater than $C_{dry}$ but smaller than $C_{wet}$ (the angle P is smallest for the rays 30a and 30n, and largest half way between them). An examination of FIGS. 1a and 1b will show that the angle P in the example described varies between 45° and about 52°. All rays 30 between 30a and 30n are thus reflected toward the photosensor 16 when the sensor surface 32 is dry (FIG. 1a), but are refracted outwardly of the body 24 when the surface 32 is wet (FIG. 1b). As the water content of the soil increases as a result of irrigation, more and more of the surface becomes wetted and thus governed by $C_{wet}$. Since P is less than $C_{wet}$, the rays striking these portions of the surface will be refracted away, reducing the number of rays traveling to the photo detector. The signal from the photosensor is proportional to the amount of rays hitting it, so it becomes also proportional to the amount of surface that is not wetted. For most types of soil, the surface of the sensor will become wetted in a piecewise continuous manner with respect to the amount of moisture in the soil. Because the sensor 10 is normally embedded in soil whose particulates attract moisture away from the surface in some proportion to the lack of moisture content in the soil, the change from reflection to refraction is not sudden but gradual with increasing moisture content of the soil. Consequently, the amount of illumination received by the photosensor 16 is a measure of soil moisture.

It will be understood that inasmuch as FIGS. 1a and 1b are axial vertical sections of the sensor 10, the rays 30 are actually half cones whose tips are at the foci 26 and 28, and whose axes are parallel to the axis A of the sensor 10. Consequently, the active or usable surface of the sensor 10 is the entire ellipsoidal surface 32 lying between the limit rays 30a and 30n which form the minimum practical angle (about 45°) with the surface 32. To facilitate manufacturing by injection molding, tapered cylindrical extensions 35 are provided on each end of the ellipsoidal portion. All rays other than those between rays 30a and 30n are reflected or refracted away from the photosensor 16.

Because humidity can over time migrate through plastic into any air gaps that may be in the light path, and because such humidity is likely to produce light-scattering beads of condensate, it is important that there be no air gap or air interface between the IRED 14 and the body 24 or between the photosensor 16 and the body 24. In order to prevent such an air gap, and in order to hold the IRED 14 and photosensor 16 in exact alignment with the body 24, the circuit board 12 of the inventive sensor 10 is entirely encapsulated within the body 24 by injection molding or another suitable manufacturing process. This is accomplished by tightly fitting the circuit board 12 into a two-piece carrier 34 (best seen in FIG. 3) which, when inserted into the mold cavity of a molding machine (not shown), prevents any movement of the circuit board 12 during the preferred injection molding process. The carrier 34 is equipped with spaced ribs 36 whose interstices allow the plastic material of the body 24 to flow freely around it during the molding process. The ribs 36 also serve to hold the carrier 34 in the molding cavity so that it cannot move during the molding operation.

In addition, care must be taken in the molding process to avoid the formation of bubbles in the area used by the light rays 30, and to make sure that the body material thoroughly "wets" the IRED 14 and photosensor 16 without any air between them, for the same reason as discussed above.

The material of the carrier 34 is preferably of a type that bonds with the material of the body 24 so as to form a tight seal with it during the molding of the body 24. The complete encapsulation of the circuit board 12 and carrier 34 also prevents any migration of moisture into the electronics if minute cracks form in the circuit board 12 due to the difference in coefficients of expansion between the circuit board material and the material of the body 24.

Figure 2A:
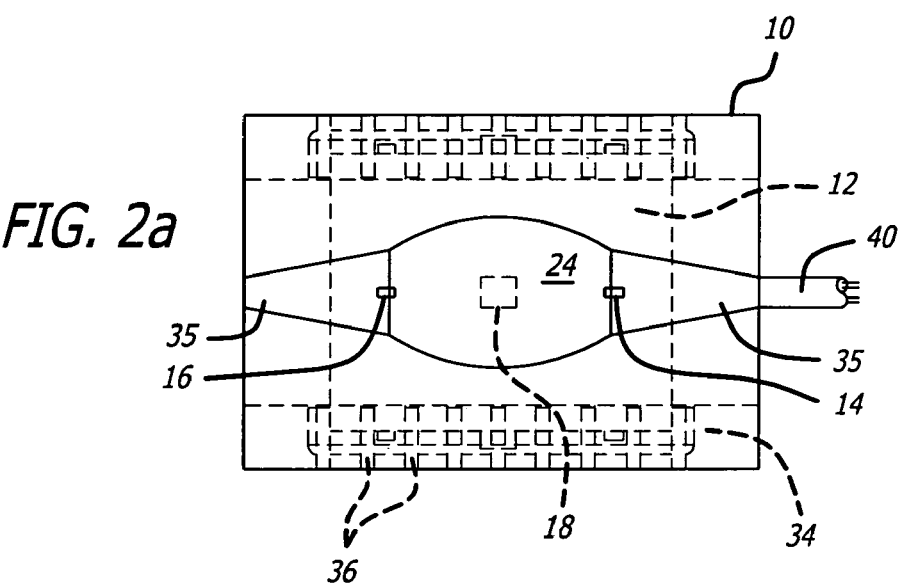
FIGS. 2a-c are top plan, end elevation and side elevation views, respectively, of the sensor encapsulated with its carrier.
Figure 2B:
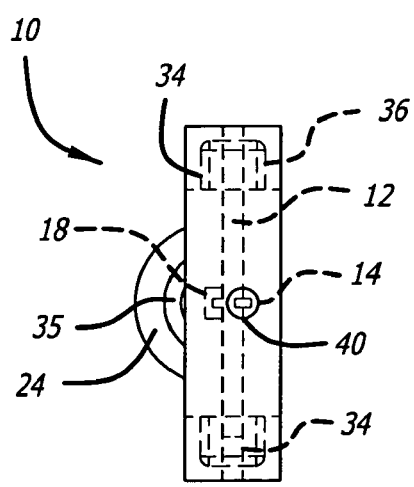
Figure 2C:
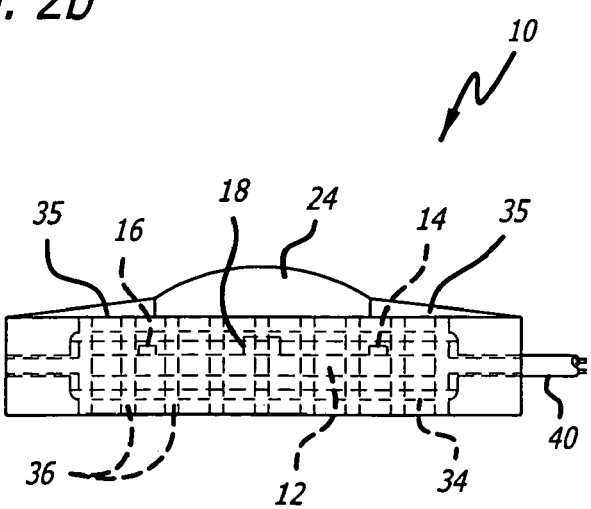
Figure 3:
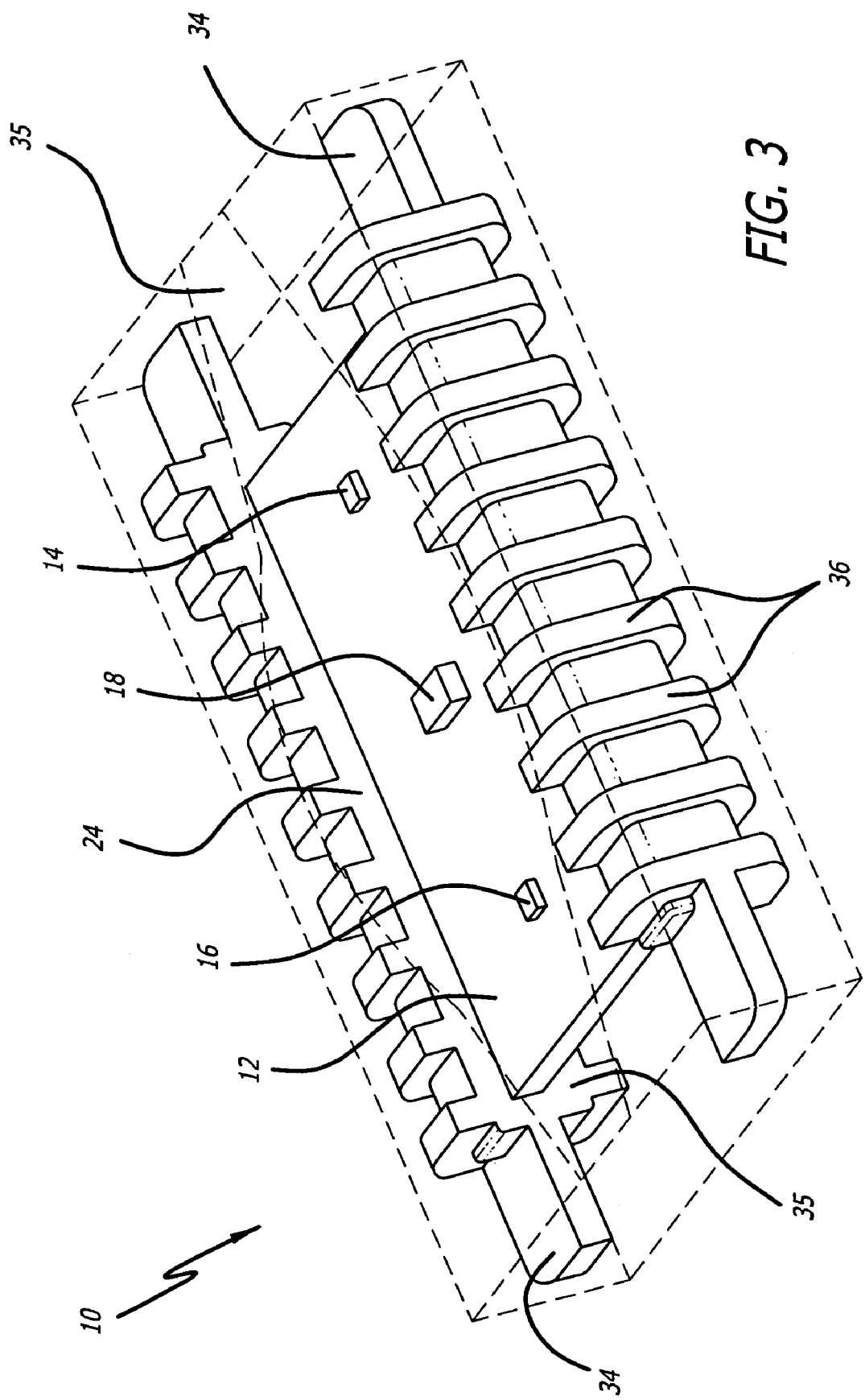
FIG. 3 is a perspective view of the finished sensor.
Figure 4:
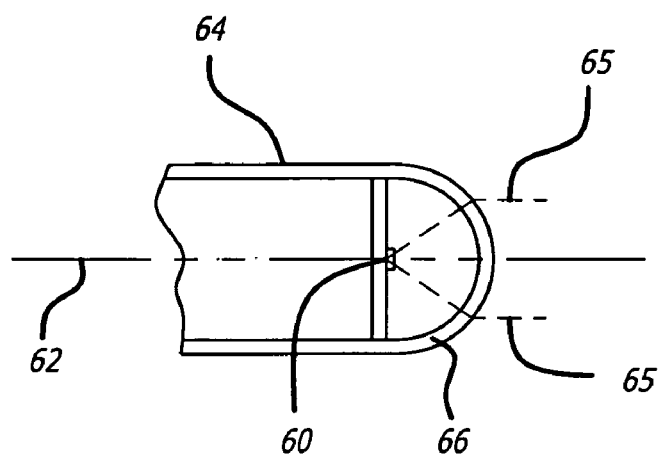
FIG. 4 is a schematic axial section of a typical spherical-nose IRED.

The molding process incorporates the circuit board 12, body 24 and carrier 34 into a monolithic sensor unit 10 shown in FIGS. 2a-c and 3 (the electrical wires interfacing the sensor 10 with external circuitry in an irrigation system are encapsulated with the circuit board 12 and are schematically shown as a cable 40 in FIGS. 2a-c; they are not shown in FIG. 3). The completed unit 10 is then usable as is without further processing. It will be understood that the circuit board 12, its solder connections and electronic components must be sufficiently heat-resistant to withstand the high temperatures encountered in injection molding.

An alternative embodiment 48 of the invention is illustrated in FIGS. 4 through 8. In that embodiment, the half-ellipsoidal body 24 is replaced with a full-ellipsoidal body 50. There is no circuit board 12, and the IRED light source 52 and photosensor 54 are mounted directly on a carrier 56 which is then encapsulated in the body 50 by injection molding or other appropriate process. The IRED light source 52 is of a type that has a current limiting resistor built into its housing, and both the IRED 52 and the photosensor 54 are equipped with a spherical lens 58. IREDs and photosensors of that construction are standard items in the industry, and are widely commercially available.

The embodiment 48 has several advantages over the embodiment 10 described above. First, the usable reflective surface of the sensor in embodiment 48 is about triple that of embodiment 10 for a given sensor size, thereby making the sensor 48 much more accurate and reliable. Secondly, the absence of a circuit board eliminates the need for caution in the molding process to avoid formation of moisture-attracting cracks in the circuit board 12 as discussed above, while at the same time reducing manufacturing costs. Also, the absence of a circuit board and the incorporation of the current-limiting resistor in the IRED assembly eliminates heat-sensitive solder joints. The IRED and photosensor assemblies have enough thermal mass to protect them against the brief thermal spike that occurs during the injection molding process.

Thirdly, as discussed in more detail below, the full encapsulation of the spherical lenses 58 dramatically reduces the direct, unreflected transmission of light from the IRED 52 to the photosensor 54, to the point where interposition of an opaque component between the IRED 52 and the photosensor 54 becomes unnecessary. Fourthly, the use of a current loop, discussed below, for conveying the output of the sensor to the electronics which use its signal, improves the sensor's resistance to noise and reduce its cost.

The essentially total elimination of direct light transfer from the IRED 52 to the photosensor 54 without any intervening light barrier, in accordance with the invention, takes advantage of the characteristic energy distribution of spherical-lens IREDs. In this type of IRED, the light source is a chip 60 (FIG. 4) that emits light mostly at about a 45 degree angle to the axis 62 of housing 64. The glass lens 66 is shaped to focus this divergent light (as e.g. at 65) toward the axis 62 when the IRED 52 is in air.

Figure 5A:
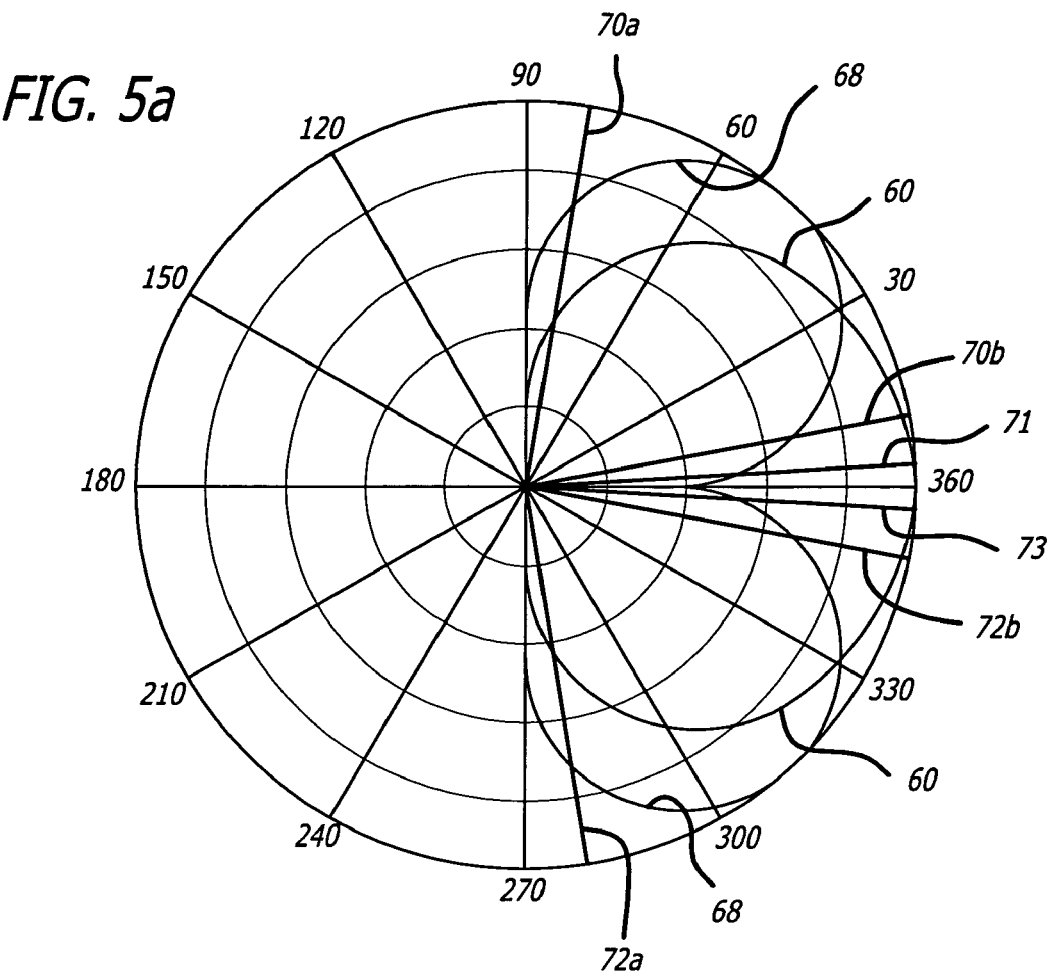
FIGS. 5a and 5b are polar and Cartesian representations, respectively, of the light energy distribution in an alternative embodiment of the invention.

Thus, in the intensity distribution diagram of FIG. 5a, curve 60 shows that the maximum light energy is emitted axially of the IRED assembly, and tapers off to zero in the direction transverse to the axis 62, when the IRED 52 is in air. When the IRED's glass lens is encapsulated, however, in a transparent material with a refractive index similar or equal to that of glass, such as COC or acrylic polymer, the focusing effect of the lens 66 is nullified, and the intensity distribution of the IRED's light becomes substantially that of curve 68. Curve 68 shows that in the encapsulation of the invention, the light intensity emitted by the IRED 52 thus peaks at about 45 degrees from the axis and is minimal in the axial and transverse directions.

As a practical matter, only light emitted at angles of about 10 degrees to 80 degrees from the axis 62 will usefully strike the surface of the body 50 and be reflected (if the surface is dry) toward the photosensor 54. Thus, the energy useful for moisture measurement in the full ellipsoid of embodiment 48 is that emitted between lines 70a and 70b, and between lines 72a and 72b, in FIG. 5a. The total quantity of useful light is a function of the toroid whose axial cross section is the area bounded by lines 70a, 70b and curve 68, and by lines 72a, 72b and curve 68.

Light emitted by the IRED 52 in a cone of about 3 degrees on each side of the axis 62, i.e. between lines 71 and 73, will strike the photosensor 54 directly. Not only is that cone very small, but the light energy within that cone, as shown by curve 68, is minimal. Mathematically, because the plot of FIG. 5a is in two-dimensional polar coordinates, the angles need to be plotted along a Cartesian axis, and the intensity needs to be multiplied by the sine of the angle to accurately represent the three-dimensional reality of the situation. This is shown in FIG. 5b.

Figure 5B:
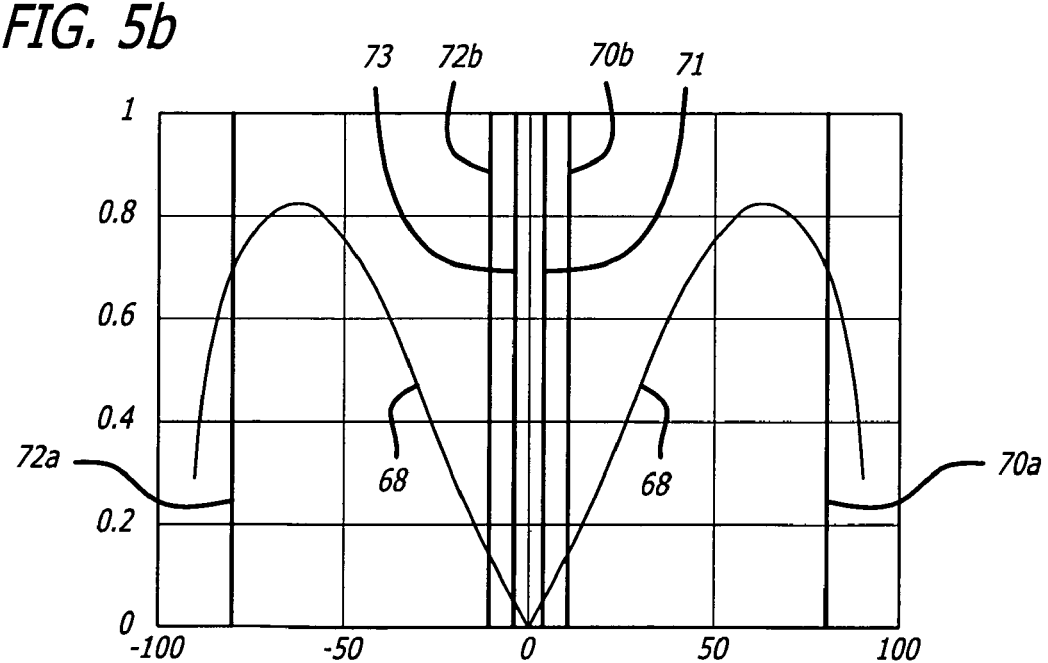
Figure 6A:
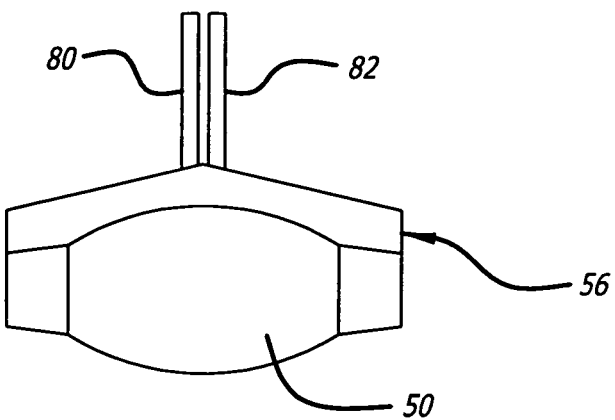
FIGS. 6a-d are plan, side, end and schematic sectional views, respectively, of the alternative embodiment.
Figure 6B:
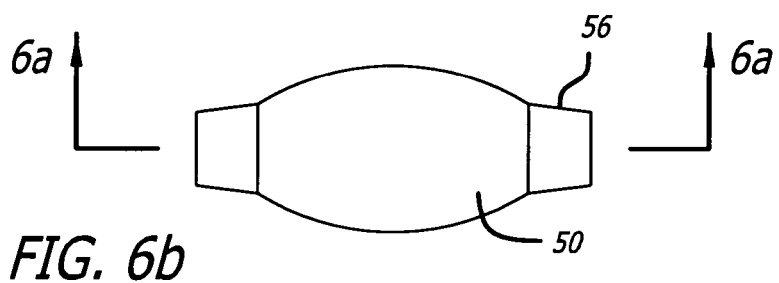
Figure 6C:
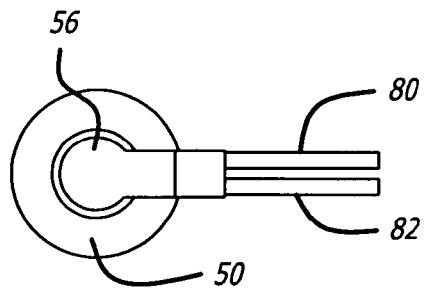
Figure 6D:
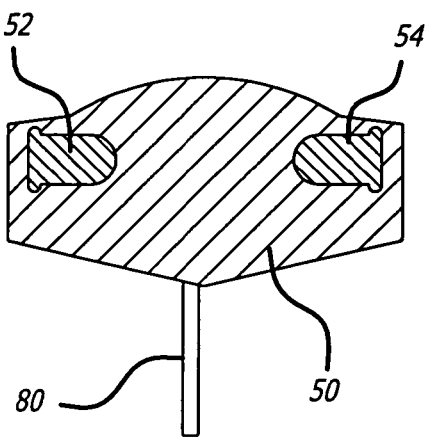

As can be seen in FIG. 5b, the ratio of direct light to reflectable light is quite dramatic. By integrating the curve 68 between lines 71 and 73, and dividing the result by the sum of the integrals of curve 68 between lines 70a and 70b, and between lines 72a and 72b, the ratio can be calculated to be approximately 0.0009. This minute error (less than 0.1%) caused by the direct illumination of the photosensor 54 is negligible for all practical purposes.

Figure 8:
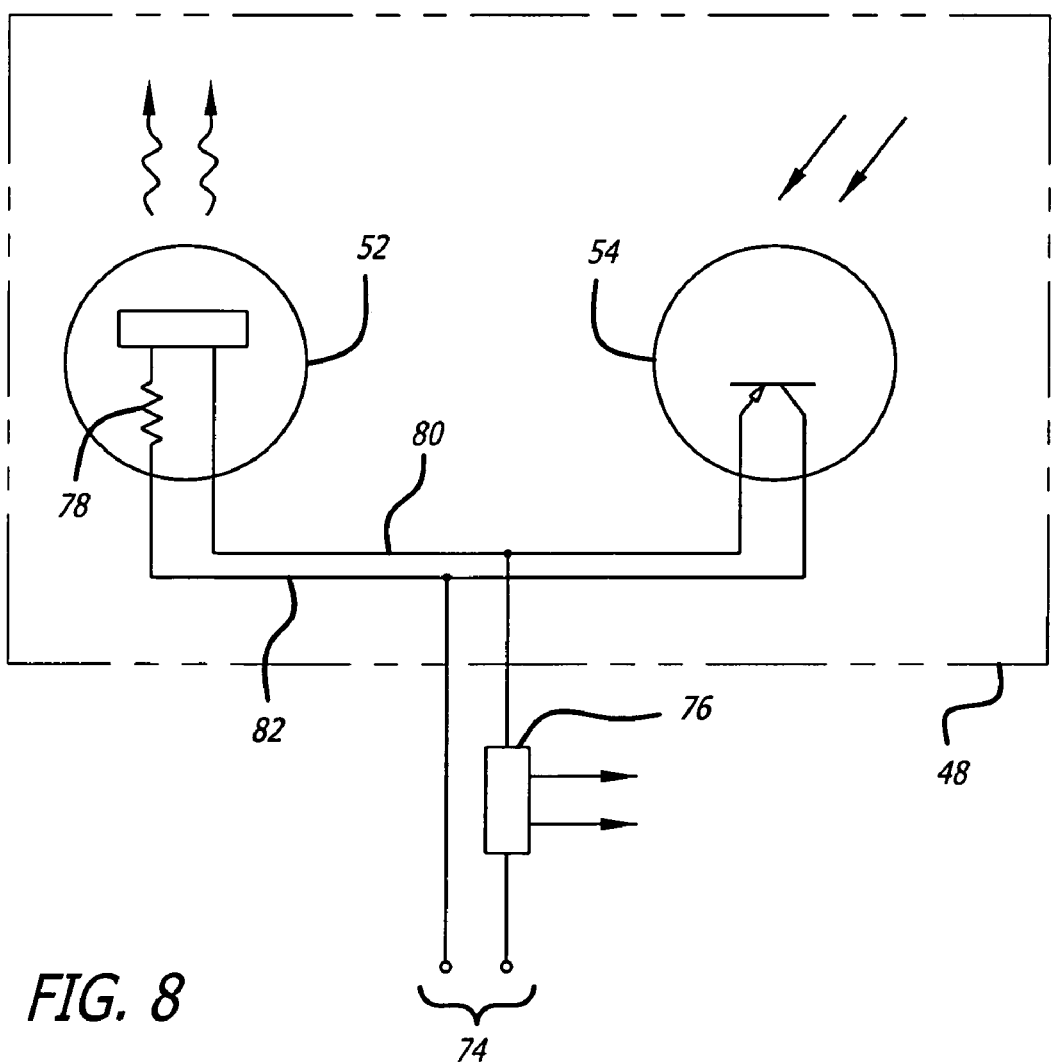
FIG. 8 is an electrical diagram of a preferred circuitry for the inventive sensor.
Figure 7:
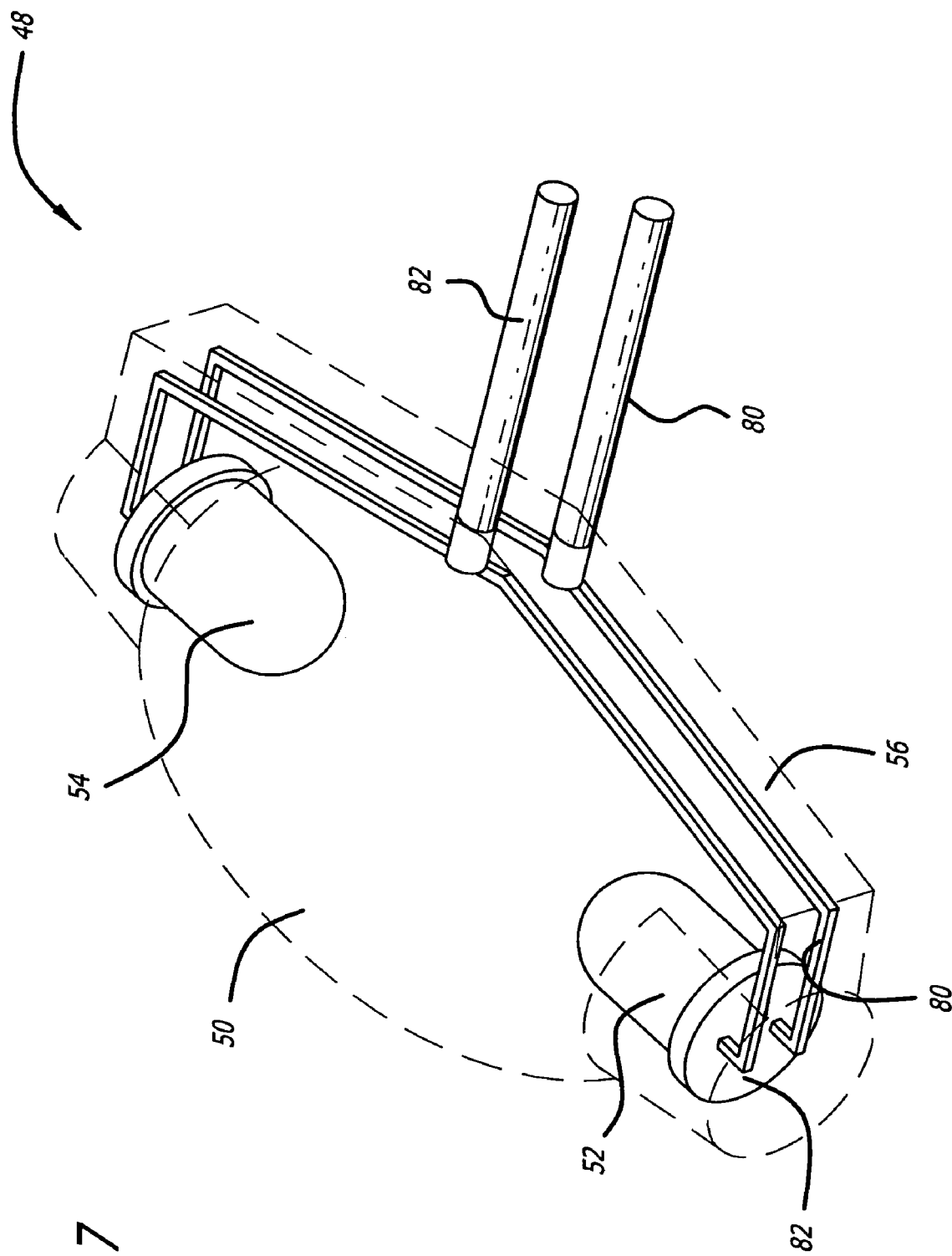
FIG. 7 is a perspective view of the alternative embodiment.

FIGS. 6a-d illustrate the ellipsoidal body 50 encapsulating the carrier 56. Shown in those figures, but better visible in FIG. 7, are the two-wire connections that connect the IRED 52 and photosensor 54 in parallel. As shown in FIG. 8, the power supply 74 for the sensor 48 is equipped with a current sensor 76 which produces the output signal of sensor 48. The current-limiting resistor 78 maintains the current drawn by the IRED 52 at a constant level, while the amount of current drawn by the photosensor 54 varies in accordance with the amount of moisture present at the surface of the body 50. By connecting the IRED 52 and photosensor 54 in parallel, a current loop is formed which requires just two wires 80, 82 in the sensor 48, instead of the conventional three or four, for cost savings and easier manufacture. Also, it has been found that the current loop approach of FIG. 8 substantially reduces the sensitivity of the sensor 48 to extraneously induced electrical noise, which has been known to be a problem in irrigation installations.

It will be understood that the above-described embodiments are only representative of the invention, and that its scope is to be limited only by the appended claims.

What is claimed is:

1. A soil moisture sensor, comprising:
   a) a solid, transparent body substantially in the shape of a half ellipsoid;
   b) a non-collimated light source positioned at a first focus of said half ellipsoid; and
   c) a photosensor positioned at a second focus of said half-ellipsoid;
   d) said light source and said photosensor being mounted on a circuit board entirely encapsulated in said body;
   e) said circuit board having at least one opaque element mounted thereon between said light source and said photosensor in such a manner as to prevent unreflected light from said light source from reaching said photosensor.

2. The sensor of claim 1, in which said opaque element is a circuit element associated with said light source or said photosensor.

3. A soil moisture sensor, comprising:
   a) a solid, transparent body substantially in the shape of a half ellipsoid;
   b) a non-collimated light source positioned at a first focus of said half ellipsoid; and
   c) a photosensor positioned at a second focus of said half-ellipsoid;
   d) said light source and said photosensor being mounted on a circuit board;
   e) a carrier holding said circuit board against movement with respect thereto;
   f) said body being part of a monolithic unit totally encapsulating said light source, photosensor, circuit board and carrier.

4. A method of making an ellipsoidal soil moisture sensor, comprising the steps of:

a) providing a carrier arranged to be firmly held in a mold cavity;

b) providing a circuit board carrying a light source and a photosensor in predetermined positions;

c) suspending said circuit board in said carrier against movement with respect thereto; and d) forming around said circuit board and carrier a monolithic, at least partially ellipsoidal, transparent body, said body totally encapsulating said circuit board and carrier therein in a position where said light source and photosensor are positioned at the foci of said ellipsoidal body;

e) the material of said body being such as to bond with the material of said carrier.

5. The method of claim 4, further comprising the step of providing on said circuit board an opaque element so positioned as to prevent the transmission of unreflected light from said light source to said photosensor.

6. The method of claim 4, in which said light source and photosensor are noncollimated.

7. The method of claim 4, in which said body is formed by injection molding, and the materials of said light source, circuit board, photosensor and carrier are chosen to withstand injection molding temperatures.

8. The method of claim 4, further comprising the step of preventing the formation of bubbles or air interfaces in the path of any light rays from said light source that are reflected toward said photosensor.

9. A soil moisture sensor, comprising:

a) a solid, transparent ellipsoidal body;

b) a non-collimated light source positioned at a first focus of said body;

c) a photosensor positioned at a second focus of said body;

d) light from said light source being reflectable toward said photosensor internally of said body when the surface of said body is dry but not when it is wet; and e) said moisture sensor being arranged to minimize transmission of unreflected light directly from said light source to said photosensor;

f) wherein said transmission is minimized by minimizing the light energy output of said light source in the direction toward said photosensor.

10. A soil moisture sensor, comprising:

a) a solid, transparent ellipsoidal body;

b) a non-collimated light source positioned at a first focus of said body;

c) a photosensor positioned at a second focus of said body;

d) light from said light source being reflectable toward said photosensor internally of said body when the surface of said body is dry but not when it is wet; and e) said moisture sensor being arranged to minimize transmission of unreflected light directly from said light source to said photosensor;

f) wherein said light source has a lens which focuses its light energy along its axis when said light source is in air, but which causes said light energy to be principally emitted away from said axis when said light source is encapsulated in a material with an index of refraction similar to that of the material of said lens.

11. A soil moisture sensor, comprising:

a) a solid, transparent ellipsoidal body;

b) a non-collimated light source positioned at a first focus of said body;

c) a photosensor positioned at a second focus of said body;

d) light from said light source being reflectable toward said photosensor internally of said body when the surface of said body is dry but not when it is wet; and e) said moisture sensor being arranged to minimize transmission of unreflected light directly from said light source to said photosensor;

f) wherein said body is in the shape of a full ellipsoid.

12. A soil moisture sensor, comprising:

a) a solid, transparent ellipsoidal body;

b) a non-collimated light source positioned at a first focus of said body;

c) a photosensor positioned at a second focus of said body;

d) light from said light source being reflectable toward said photosensor internally of said body when the surface of said body is dry but not when it is wet; and e) said moisture sensor being arranged to minimize transmission of unreflected light directly from said light source to said photosensor;

f) wherein said light source and photosensor are connected in parallel to form a current loop.

* * * * *